(12) United States Patent
Chilukuri

(10) Patent No.: US 12,073,946 B2
(45) Date of Patent: Aug. 27, 2024

(54) METHODS AND APPARATUS FOR ARTIFICIAL INTELLIGENCE MODELS AND FEATURE ENGINEERING TO PREDICT EVENTS

(71) Applicant: ZS Associates, Inc., Evanston, IL (US)

(72) Inventor: Srinivas Sainaga Chilukuri, Buffalo Grove, IL (US)

(73) Assignee: ZS Associates, Inc.

( * ) Notice: Subject to any disclaimer, the term of this patent is extended or adjusted under 35 U.S.C. 154(b) by 353 days.

(21) Appl. No.: 17/517,863

(22) Filed: Nov. 3, 2021

(65) Prior Publication Data
US 2022/0139559 A1 May 5, 2022

Related U.S. Application Data

(60) Provisional application No. 63/110,202, filed on Nov. 5, 2020.

(51) Int. Cl.
*G16H 50/20* (2018.01)
*G06N 3/126* (2023.01)
*G16H 50/30* (2018.01)
*G16H 50/70* (2018.01)

(52) U.S. Cl.
CPC .............. *G16H 50/20* (2018.01); *G06N 3/126* (2013.01); *G16H 50/30* (2018.01); *G16H 50/70* (2018.01)

(58) Field of Classification Search
CPC ........ G16H 50/20; G16H 50/70; G16H 50/30; G06N 3/126
See application file for complete search history.

(56) References Cited

PUBLICATIONS

Zhang et al., MetaPred: Meta-Learning for Clinical Risk Prediction with Limited Patient Electronic Health Records, Applied Data Science Track Paper 2487-2495 (Aug. 9, 2019) (Year: 2019).*
Wang et al., Rule induction for forecasting method selection: Meta-learning the characteristics of univariate time series, 72(10-12) Neurocomputing 2581-2594 (Jun. 2009) (Year: 2009).*

(Continued)

*Primary Examiner* — Jordan L Jackson
(74) *Attorney, Agent, or Firm* — Foley & Lardner LLP

(57) ABSTRACT

Provided herein are methods and systems for selecting featured within high dimensional datasets to predict an event. In one embodiment, a method comprises determining, by a processor, a probability of occurrence of one or more features within a high dimensional patient dataset; profiling, by the processor, the one or more features in accordance with their respective probability of occurrence; executing, by the processor, a feature generation model to select at least one feature from the profiled features and a corresponding time window for the at least one feature; executing, by the processor, a time search model to select at least one time interval from a set of time intervals that includes time intervals associated with the profiled features or the at least one feature; executing, by the processor, a meta-learning model to calculate a fitness score based on the at least one feature and the at least one time interval; and using, by the processor, responsive to the at least one feature having the fitness score that satisfies a threshold, the at least one feature to predict an event associated with a patient.

20 Claims, 7 Drawing Sheets

(56) References Cited

PUBLICATIONS

Rudovic et al., Meta-Weighted Gaussian Process Experts for Personalized Forecasting of AD Cognitive Changes, 106 Proceedings of Machine Learning Research 1-15 (2019) (Year: 2019).*

Choi et al., Using recurrent neural network models for early detection of heart failure onset, 24(2) J of the American Medical Informatics Association 361-370 (2017) (Year: 2017).*

Q Wang and Megalooikonomou, A Dimensionality Reduction Technique for Efficient Time Series Similarity Analysis, 33(1) Inf System. 115-132 (Year: 2008).*

Anonymous: "Feature extraction—Wikipedia", Aug. 27, 2020 (Aug. 27, 2020), XP055901883, Retrieved from the Internet: URL:https://en.wikipedia.org/w/index.php?title=Feature_extraction&oldid=975289468 [retrieved on Mar. 16, 2022].

Anonymous: "Feature selection—Wikipedia", Oct. 13, 2019 (Oct. 13, 2019), XP055788078, Retrieved from the Internet: URL:https://en.wikipedia.org/w/index.php title=Feature selection&oldid=920990787 [retrieved on Mar. 22, 2021].

Foreign Search Report on EP 21206673.2 DTD Mar. 24, 2022.

Mortazavi Bobak Jet al: "Prediction of Adverse Events in Patients Undergoing Major Cardiovascular Procedures", IEEE Journal of Biomedical and Health Informatics, IEEE, Piscataway, NJ, USA, vol. 21, No. 6, Nov. 1, 2017 (Nov. 1, 2017), pp. 1719-1729.

\* cited by examiner

200

```
┌─────────────────────────────────────────────────────────────────┐
│  Receive high dimensional patient data that include a set of    │
│  base features 201                                              │
└─────────────────────────────────────────────────────────────────┘
                               │
┌─────────────────────────────────────────────────────────────────┐
│  Associate an occurrence probability to each base feature of    │
│  the high dimensional patient data to generate a set of         │
│  profiled base features 202                                     │
└─────────────────────────────────────────────────────────────────┘
                               │
┌─────────────────────────────────────────────────────────────────┐
│  Execute a time search model to select at least one time        │
│  interval from a set of time intervals, each time interval      │
│  rolling up a subset of profiled base features 203              │
└─────────────────────────────────────────────────────────────────┘
                               │
┌─────────────────────────────────────────────────────────────────┐
│  Execute a feature selection model to select at least one       │
│  feature from the set of profiled base features, the feature    │
│  selection model having a feature store 204                     │
└─────────────────────────────────────────────────────────────────┘
                               │
┌─────────────────────────────────────────────────────────────────┐
│  Execute a meta-learning model to calculate a fitness value     │
│  based on the at least one feature and the at least one time    │
│  interval 205                                                   │
└─────────────────────────────────────────────────────────────────┘
                               │
┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┐
│  Execute a classifier to predict an importance score for the    │
│  at least one feature 206                                       │
└─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
```

Profiling one or more features within a high dimensional patient dataset in accordance with their respective probability of occurrence. 701

Selecting at least one feature from the profiled features and a corresponding time window for the at least one feature. 702

Selecting at least one time interval that includes time intervals associated with the profiled features or the at least one feature. 703

Calculating a fitness value based on the at least one feature and the at least one time interval. 704

Using the at least one feature to predict an event associated with a patient when the at least one feature satisfies a threshold. 705

FIG. 7

METHODS AND APPARATUS FOR ARTIFICIAL INTELLIGENCE MODELS AND FEATURE ENGINEERING TO PREDICT EVENTS

CROSS-REFERENCE TO RELATED APPLICATIONS

This application claims priority to U.S. Provisional Patent Application No. 63/110,202, filed Nov. 5, 2020, which is incorporated herein by reference in its entirety for all purposes.

TECHNICAL FIELD

The present disclosure relates to the field of artificial intelligence and knowledge processing systems for generating features and predicting events using multidimensional datasets.

BACKGROUND

Patient journey event prediction can be useful in a range of applications, such as site selection for clinical trials, targeting patients, educating opinion leaders, performing predictive customer targeting, improving and optimizing patient services, improving and optimizing patient adherence, and the like. With increasing generation and access to patient journey event data enabled by recent advances in electronics, telecommunication, and the availability of the Internet, predicting a patient's journey (e.g., predicting event associated with the patient) is an increasingly important task. Some conventional methods, however, involve performing manual tasks or do not effectively use real-world data that are high dimensional, large in volume, and rich in details. Therefore, these conventional methods result in sub-optimal feature generation and/or results.

Typically, when performing the analysis manually, various data patterns cannot be uncovered and are missed by human reviewers. To rectify this problem, some conventional methods use artificial intelligence-based solutions, such as deep learning models, to analyze high-dimensional patient data to identify insights. However, these methods often fall short in performance when using high dimensional data because high dimensional data is computationally intensive to analyze. Using a brute force method (e.g., analyzing most or all permutations) can lead to untimely and inefficient results while artificially excluding portions of a high dimensional dataset can lead to erroneous or incomplete results.

SUMMARY

For the aforementioned results, a need exists for efficient (e.g., reducing time and computing resources needed) and scalable (e.g., capable of processing large volume of data) apparatus, methods, and systems to automate patient journey event prediction using high dimensional and high volume data. Using the methods and systems described herein, a processor can utilize various modeling techniques to identify features within a high dimensional dataset that are more likely to contribute to an accurate prediction. Using the methods and system described herein, a processor can also identify a time interval corresponding to the identified features that can provide patient data that could lead to accurate predictions. The methods and systems described herein then analyze the identified features within the proper time intervals to predict various patient journey events or patient events.

Using the methods and systems described herein, a machine learning model can be trained using a portion of a training dataset that is down-sampled based on the identification of a subset of features calculated to yield accurate results. Because the revised training dataset does not include all the features within a high dimensional patient data but includes only the relevant portions that could produce efficient results, the machine learning model can be executed or trained more efficiently (e.g., without needing high computing power while producing more timely results).

In some embodiments, a method can include receiving high dimensional patient data that include a set of base features (e.g., diagnoses, medications, procedures, etc.). The method can further include associating an occurrence probability to each base feature of the high dimensional patient data to generate a set of profiled base features. The method can further include executing a time search model to select at least one time interval from a set of time intervals, each time interval rolling-up and/or including a subset of profiled base features. The method can further include executing a feature selection model to select at least one feature from the set of profiled base features, the feature selection model having access to and/or storing data in a feature store (e.g., of a memory). The method can further include executing a meta-learning model to calculate a fitness score based on the at least one feature and the at least one time interval.

In an embodiment, a method comprises determining, by a processor, a probability of occurrence of one or more features within a high dimensional patient dataset; profiling, by the processor, the one or more features in accordance with their respective probability of occurrence; executing, by the processor, a feature generation model to select at least one feature from the profiled features and a corresponding time window for the at least one feature; executing, by the processor, a time search model to select at least one time interval from a set of time intervals that includes time intervals associated with the profiled features or the at least one feature; executing, by the processor, a meta-learning model to calculate a fitness score based on the at least one feature and the at least one time interval; and using, by the processor, responsive to the at least one feature having the fitness score that satisfies a threshold, the at least one feature to predict an event associated with a patient.

The method may also comprise executing, by the processor, a classifier to predict an importance score for the at least one feature.

The method may also comprise training, by the processor, a machine learning model to predict an importance score for the at least one feature.

The feature generation model may comprise a feature store configured to store the at least one feature.

The meta-learning model may iteratively calculate the fitness score for the at least one feature for each time interval within the set of time intervals.

The high dimensional patient dataset may comprise data associated with one or more patient journey events comprising at least one of a doctor visit, a lab test, a pharmacy prescription, a hospitalization record, a diagnosis, a medication, or a procedure associated with the patient.

The feature generation model may use a recency aggregator indicating a time since last occurrence of the at least one feature within the high dimensional patient dataset.

The feature generation model may use a count aggregator indicating a number of occurrences of the at least one feature within the high dimensional patient dataset.

The feature generation model may comprise a genetic algorithm.

In another embodiment, a computer system comprises a server having a processor to communicate with a data repository storing a high dimensional patient dataset, the server configured to: determine a probability of occurrence of one or more features within the high dimensional patient dataset; profile the one or more features in accordance with their respective probability of occurrence; execute a feature generation model to select at least one feature from the profiled features and a corresponding time window for the at least one feature; execute a time search model to select at least one time interval from a set of time intervals that includes time intervals associated with the profiled features or the at least one feature; execute a meta-learning model to calculate a fitness score based on the at least one feature and the at least one time interval; and use, responsive to the at least one feature having the fitness score that satisfies a threshold, the at least one feature to predict an event associated with a patient.

The server may be further configured to execute a classifier to predict an importance score for the at least one feature.

The server may be further configured to train a machine learning model to predict an importance score for the at least one feature.

The feature generation model may comprise a feature store configured to store the at least one feature.

The meta-learning model may iteratively calculate the fitness score for the at least one feature for each time interval within the set of time intervals.

The high dimensional patient dataset may comprise data associated with one or more patient journey events comprising at least one of a doctor visit, a lab test, a pharmacy prescription, a hospitalization record, a diagnosis, a medication, or a procedure associated with the patient.

The feature generation model may use a recency aggregator indicating a time since last occurrence of the at least one feature within the high dimensional patient dataset.

The feature generation model may use a count aggregator indicating a number of occurrences of the at least one feature within the high dimensional patient dataset.

The feature generation model may comprise a genetic algorithm.

In yet another embodiment, a computer system comprises a server comprises a processor and a non-transitory computer-readable medium containing instructions that when executed by the processor causes the processor to perform operations comprising: determining a probability of occurrence of one or more features within a high dimensional patient dataset; profiling the one or more features in accordance with their respective probability of occurrence; executing a feature generation model to select at least one feature from the profiled features and a corresponding time window for the at least one feature; executing a time search model to select at least one time interval from a set of time intervals that includes time intervals associated with the profiled features or the at least one feature; executing a meta-learning model to calculate a fitness score based on the at least one feature and the at least one time interval; and using responsive to the at least one feature having the fitness score that satisfies a threshold, the at least one feature to predict an event associated with a patient.

The instructions may further cause the processor to execute a classifier to predict an importance score for the at least one feature.

BRIEF DESCRIPTION OF THE DRAWINGS

FIG. 2 is a flowchart illustrating a method for patient journey event prediction, according to an embodiment.

FIG. 7 is a flowchart illustrating a method for patient journey event prediction, according to an embodiment.

DETAILED DESCRIPTION

Figure 1:
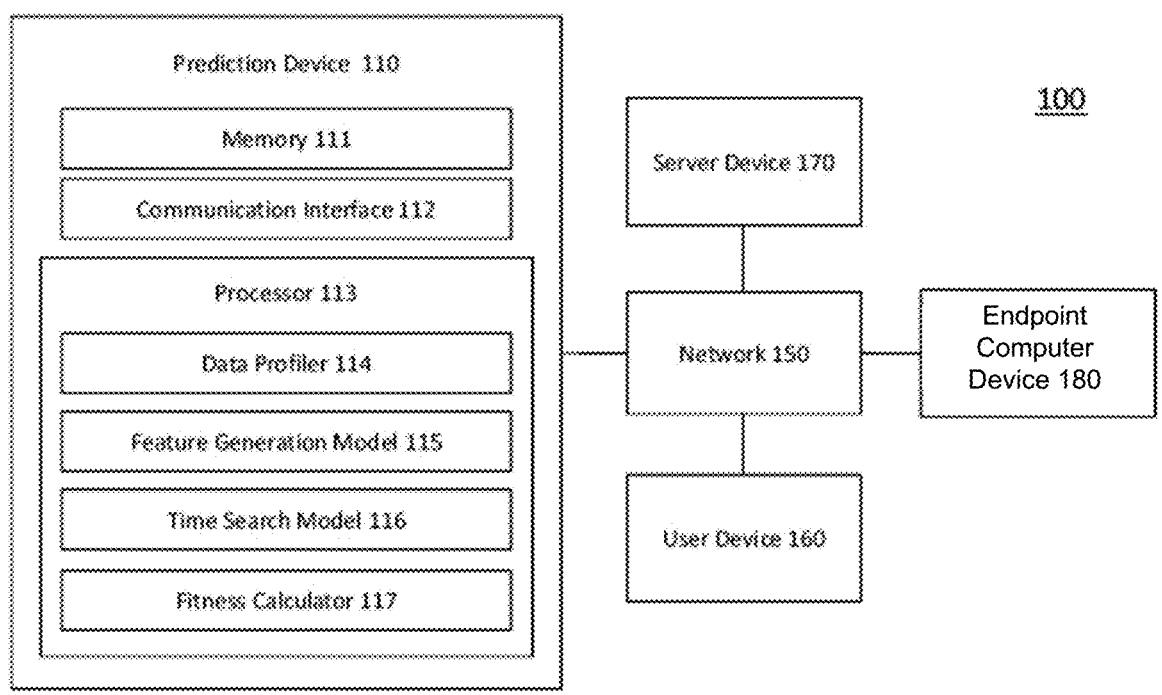
FIG. 1 is a schematic illustration of a prediction device, according to an embodiment.

Non-limiting examples of various aspects and variations of the embodiments are described herein and illustrated in the accompanying drawings.

One or more embodiments described herein generally relate to apparatus, methods, and systems for dynamically processing structured and semi-structured data. In particular, apparatus, methods, and systems described herein use a feature generation model and a time search model to efficiently and reliably select features and time intervals within the structured and semi-structured data. Apparatus, methods and systems for patient journey event prediction are disclosed. In some embodiments, patient journey event prediction can be used to process, for example, longitudinal patient data (e.g., real world data, electronic health record (EHR), administrative claims, clinical trial activity data and/or the like) in form of time series including, stationary data, non-stationary-data, linear data, non-linear data, seasonal data, periodic data, chaotic data, univariate data, multivariate data, and/or the like. The longitudinal patient data can be high dimensional, high volume, and rich in details.

Described herein are prediction devices that use suitable models on high dimensional and high volume data for reliable feature generation and predicting patient journey events. One or more prediction devices described herein include a genetic algorithm model and a gradient boosted tree model. A stand-alone genetic algorithm model can be used for solving constrained and/or unconstrained optimization problems based on natural selections in data, and therefore can become time-consuming and as a result fail when the data becomes increasingly large. The genetic algorithm model described herein includes a memory component that avoids generating duplicate features by the genetic algorithm model. Moreover, execution of the genetic algorithm model with the gradient boosted tree model can process the high dimensional and high volume data that could not be effectively processed using deep learning methods or genetic algorithm models alone. Use of the genetic algorithm model with the gradient boosted tree model in the one or more prediction devices described herein enables the genetic algorithm model to effectively process high dimensional and high volume data, and to generate a set of features that are eventually used to predict patient journey events. The genetic algorithm models described herein can increase the efficient generation of the set of features from the high dimensional and high volume data.

Embodiments described herein provide methods and systems for generating features such as, for example, features associated with medical records, features associated with time, features associated with laboratory results, features associated with locations, features associated with environmental factors (e.g., temperature, humidity, etc.), features associated with economic indicators, features associated with social factors, and/or the like. In some instances, the features can include text data, numerical data, symbolic data, and/or the like.

While the methods and apparatus are described herein as processing data from a set of files, a set of tables, a set of documents, a set of databases, and/or the like, in some instances a prediction device (e.g., prediction device 110 shown and described herein with respect to FIG. 1) can be used to generate the set of files, the set of tables, the set of documents, the set of databases and/or the like. Therefore, the prediction device can be used to process and/or generate any collection or stream of data, events, and/or objects. As an example, the prediction device can process and/or generate any string(s), number(s), image(s), video(s), executable file(s), dataset(s), Uniform Resource Locator (URL), global positioning system (GPS) data, name(s), address(es), telephone number(s), email address(es), and/or the like. For further examples, the prediction device can be used to execute or process an application programming interface (API), a function(s) of a software code(s), a webpage(s), a data file(s), a data stream(s), a model file(s), a source file(s), a script(s), a table(s) in a database system, a document-processing macro(s), an e-mail message(s), a text message(s), and/or the like.

FIG. 1 is a schematic illustration of a prediction system 100, according to an embodiment. The prediction system 100 can include a prediction device 110, a user device 160, a server device 170, and an endpoint computer device 180. These features are operatively coupled and communicate via a network 150. The prediction device 110 includes a memory 111, a communication interface 112, and a processor 113 and can be used to receive and process high dimensional and high volume data. The prediction device 110 can be used to generate or select a set of features in the high dimensional and high volume data. The set of features can be used to predict patient journey events (e.g., doctor visits, lab results, hospitalization, medication, and/or the like). In one example, the prediction device 110 can receive medical records, financial records, and/or social records of a patient and generate a recommendation for a medical checkup, medical treatment, medical products, and/or the like. In another example, the prediction device 110 can receive medical records, financial records, performance records, and/or social records of employees of an organization and generate a prediction for such employees (e.g., an estimated number of diabetic employees in the next fiscal year).

The memory 111 of the prediction device 110 can be, for example, a memory buffer, a random access memory (RAM), a read-only memory (ROM), a hard drive, a flash drive, a secure digital (SD) memory card, a compact disk (CD), an external hard drive, an erasable programmable read-only memory (EPROM), an embedded multi-time programmable (MTP) memory, an embedded multimedia card (eMMC), a universal flash storage (UFS) device, and/or the like. The memory 111 can store, for example, one or more software modules and/or code that includes instructions to cause the processor 113 to execute one or more processes or functions (e.g., a data profiler 114, a feature generation model 115, a time search model 116, and/or a fitness calculator 117).

The memory 111 can store a set of files associated with (e.g., generated by executing) a feature generation model 115 and/or a time search model 116. The set of files associated with the feature generation model 115 and/or the time search model 116 can include data generated by the feature generation model 115 and/or the time search model 116 during the operation of the prediction device 110. For example, the set of files associated with the feature generation model 115 and/or the time search model 116 can include temporary variables, return memory addresses, variables, a graph of the feature generation model 115, and/or the time search model 116 (e.g., a set of arithmetic operations or a representation of the set of arithmetic operations used by the feature generation model 115 and/or the time search model 116), the graph's metadata, assets (e.g., external files), electronic signatures (e.g., specifying a type of the feature generation model 115 and/or the time search model 116 being exported, and the input/output arrays and/or tensors), and/or the like, generated during the operation of the feature generation model 115 and/or the time search model 116.

The communication interface 112 of the prediction device 110 can be a software component (e.g., executed by processor 113) or a hardware component of the prediction device 110 to facilitate data communication between the prediction device 110 and external devices (e.g., the user device 160, the server device 170, the endpoint computer device 180, and/or the like) or internal components of the prediction device 110 (e.g., the memory 111, the processor 113). The communication interface 112 is operatively coupled to and used by the processor 113 and/or the memory 111. The communication interface 112 can be, for example, a network interface card (NIC), a Wi-Fi™ module, a Bluetooth® module, an optical communication module, and/or any other suitable wired and/or wireless communication interface. The communication interface 112 can be configured to connect the prediction device 110 to the network 150, as described in further detail herein. In some instances, the communication interface 112 can facilitate receiving or transmitting data via the network 150.

More specifically, in some implementations, the communication interface 112 can facilitate receiving or transmitting high dimensional and high volume data, the set of features, the feature generation model 115 the time search model 116, and/or the like through the network 150 from/to the user device 160, the server device 170, and/or the endpoint computer device 180, each of which is communicatively coupled to the prediction device 110 via the network 150. In some instances, data received via communication interface 112 can be processed by the processor 113 and/or stored in the memory 111, as described in further detail herein.

The processor 113 can be, for example, a hardware-based integrated circuit (IC) or any other suitable processing device configured to run or execute a set of instructions or a set of code. For example, the processor 113 can include a general-purpose processor, a central processing unit (CPU), an accelerated processing unit (APU), an application-specific integrated circuit (ASIC), a field-programmable gate array (FPGA), a programmable logic array (PLA), a complex programmable logic device (CPLD), a programmable logic controller (PLC), a graphics processing unit (GPU), a neural network processor (NNP), and/or the like. The processor 113 can be operatively coupled to the memory 111 through a system bus (for example, address bus, data bus, and/or control bus, not shown).

The prediction device 110 can be operatively coupled to the user device 160, the server device 170, and/or the endpoint computer device 180 to receive and/or transmit data and/or analytical models via the network 150. A user of the user device 160 and/or a clinician using the endpoint computer device 180 can use the prediction device 110 to obtain a patient journey event prediction. In some instances, the user device 160 and/or the clinician device can send patient data to the prediction device 110 and receive a prediction and/or a set of selected features for the prediction of the patient journey event. The server device 170 can be used by the prediction device for data storage and/or data analytics (e.g., via an application programming interface (API)). The prediction device 110, the user device 160, the server device 170, and/or the endpoint computer device 180 each can include a hardware-based computing device and/or a multimedia device. In some embodiments, the prediction device 110 can use computing resources of the server device 170 to perform one or more computing tasks such as, for example, the feature generation model 115 and/or the time search model 116.

The network 150 can be a digital telecommunication network of servers and/or computer devices discussed herein. The servers and/or computer devices on the network can be connected via one or more wired or wireless communication networks (not shown) to share resources such as, for example, data storage and/or computing power. The wired or wireless communication networks between servers and/or computer devices of the network 150 can include one or more communication channels, for example, a radio frequency (RF) communication channel(s), an extremely low frequency (ELF) communication channel(s), an ultra-low frequency (ULF) communication channel(s), a low frequency (LF) communication channel(s), a medium frequency (MF) communication channel(s), an ultra-high frequency (UHF) communication channel(s), an extremely high frequency (EHF) communication channel(s), a fiber optic commination channel(s), an electronic communication channel(s), a satellite communication channel(s), and/or the like. The network 150 can be, for example, the Internet, an intranet, a local area network (LAN), a wide area network (WAN), a metropolitan area network (MAN), worldwide interoperability for microwave access network (WiMAX®), a virtual network, any other suitable communication system and/or a combination of such networks.

The user device 160 and/or the endpoint computer device 180 can be/include computer devices operatively coupled and configured to transmit and/or receive data and/or analytical models to the prediction device 110. The endpoint computer device 180 can be or include, for example, a clinician platform, an electronic health record (HER) device, a hospital computer device, insurance provider computer device, pharmaceutical company computer device, researcher computer device, and/or the like. A user of user device 160 and/or the endpoint computer device 180 can use the prediction device 110 (partially or fully) for a patient journey event prediction. In some instances, the user device 160 and/or the endpoint computer device 180 can be/include, for example, a personal computer, a laptop, a smartphone, a custom personal assistant device, and/or the like, each including a memory (not shown), a communication interface (not shown) and/or a processor (not shown).

The processor of the user device 160 and/or the endpoint computer device 180 can include a hardware-based integrated circuit (IC) or any other suitable processing device configured to run and/or execute a set of instructions or code. The memory of the user device 160 and/or the endpoint computer device 180 can include a hardware-based charge storage electronic device or any other suitable data storage medium configured to store data for long term or batch processing of the data by the processor. The communication interface of the user device 160 and/or the endpoint computer device 180 can include a hardware-based device configured to receive/transmit electric signals, electromagnetic signals, and/or optical signals.

The server device 170 can be/include computer device mediums specialized for data storage purposes and/or computing purposes that can include, for example, a network of electronic memories, a network of magnetic memories, a server(s), a blade server(s), a storage area network(s), network-attached storage(s), deep learning computing servers, deep learning storage servers, and/or the like. Each server device 170 can include a memory (not shown), a communication interface (not shown), and/or a processor (not shown). The memory can store the data, the processor can analyze the data, and the communication interface can receive/transmit the data from/to the prediction device 110 via the network 150.

The processor 113 can include a data profiler 114, a feature generation model 115, a time search model 116, and a fitness calculator 117. Each of the data profiler 114, the feature generation model 115, the time search model 116, and the fitness calculator 117 can include software stored in the memory 111 and executed by the processor 113. For example, a code to cause the data profiler 114 to fetch/process the high dimensional and high volume data can be stored in the memory 111 and executed by the processor 113. Alternatively, each of the data profiler 114, the feature generation model 115, the time search model 116, and the fitness calculator 117 can be a hardware-based device. For example, a process to cause the fitness calculator 117 to generate a fitness score for a set of selected features can be implemented on an individual integrated circuit chip (e.g., an ASIC).

The data profiler 114 can be used to receive the data (e.g., high dimensional and high volume data) for analysis by the processor 113 and/or profile the data. In some instances, the data can include temporal data that includes time series and/or information that is associated with time stamps. For example, the data can include medical records of a patient where each medical record is associated with a time stamp. In another example, the data can include a signal about the patient's neural activity recorded by an implant. Such signals can be continuously, periodically and/or sporadically received by the prediction device 110 as a stream of data while the prediction device 110 is, directly and/or via an intermediate device (e.g., the user device 160), coupled to the implant directly. In some instances, the data can also include location and/or vendor data. For example, the data can include cardiovascular data recorded by an indicated medical device made by a vendor in an identified hospital (e.g., George Washington University hospital, Tokyo hospital, and/or the like) of an identified city (e.g., Washington, Tokyo, and/or the like) at an indicated time (e.g., a year, a day, an hour, and/or the like).

Profiling the data using the data profiler 114 can involve finding a frequency of occurrence and consequently an occurrence probability for base features in the data to generate profiled base features. The profiled base features can include the base features each associated with a probability. Profiling the set of base features in the data to generate the set of profiled base features can reduce the selection time of the feature generation model 115 by starting with a base feature that has a high likelihood of being a good predictor of the patient journey events.

In some embodiments, the profiled base features can be prepared (e.g., by the data profiler 114) to be used by the feature generation model 115 and/or the time search model 116. In some instances, the data profiler 114 can normalize the profiled base features to a common scale. Normalization can involve transforming data into a common format to improve cross-compatibility of the data or the set of features among various modules of the prediction device 110 including the feature generation model 115 and/or the time search model 116. In some instances, the data profiler 114 can format a set of data files that contain the profiled base features to a common character format such as American Standard Code for Information Interchange (ASCII) format, Unicode format, and/or the like. In some instances, the data profiler 114 can format a set of data files that contain the data to comma-separated values (CSV) file formats. In some instances, the data profiler 114 can include the occurrence probability for each feature of the data and can normalize the occurrence probability of the features to a common range from 0 to 1.

The feature generation model 115 can be used to generate or select at least one feature from the set of profiled base features. The feature generation model can include/access a feature store (e.g., as part of the memory 111). In some configurations, the feature generation model (e.g., an integrated circuit performing the feature generation model) can include the feature store (e.g., a local memory) to store generated and/or selected features. In some configurations, the feature generation model (e.g., a code stored in the memory 111 to instruct the processor 113) can access the feature store (e.g., using a memory address) to store generated and/or selected features. The feature generation model can involve executing a genetic algorithm. The genetic algorithm can include parameters such as, for example, a maximum number of generations, a fitness threshold, and/or the like. In some instances, the parameters can be calculated/determined based on heuristics observed across several experiments (e.g., several executions of the genetic algorithm). The feature store of the feature generation model 115 can include a memory and/or a memory allocation to store previously generated or selected features and help the convergence of the feature generation model 115.

The time search model 116 can be/include a hierarchical time interval selection model executed on patient journey event data that has a temporal nature. The patient journey event data can include time series and/or events that are associated with a timestamp. The time search model 116 can select at least one-time interval from a set of time intervals, each time interval rolling up/aggregating base features and/or profiled base features from time intervals associated with such base features. The hierarchical time search model can involve selecting time intervals in granular levels and/or time periods (e.g., year, season, month, day, etc.) of the patient journey events data. The time search model 116 can be and/or include a binary tree search that propagates across the granularity levels. Doing so can reduce the number of iterations needed for convergence of the time search model 116 for selecting at least one-time interval.

The fitness calculator 117 calculates a fitness score based on at least one feature generated or selected by the feature generation model 115 and/or the at least one-time interval selected by the time search model 116. A meta-learning model of the fitness calculator 117 can involve calculating an adjusted odds ratio to evaluate a relative fitness of a variable such as at least one feature and/or at least one-time interval. The adjusted odds ratio can be calculated by the following equation:

$$AOR = \frac{p(\text{feature, event} = 1)/p(\text{event} = 1)}{p(\text{feature, event} = 0)/p(\text{event} = 0)}$$

where AOR represents the adjusted odds ratio. Here, an odds ratio (the numerator of the equation) is a statistical measure that a selection of at least one feature in the at least one-time interval results incorrectly predicting an event happening as opposed to the event not happening. The adjusted odds ratio is the normalized form of the odds ratio that is distributed between 0 and 1.

In some implementations, the meta-learning model can be calculated as a weighted average of multiple scores including the adjusted odds ratio, statistical information gain measures at a feature level (e.g., Gini index, Analysis of Variance (ANOVA), etc.) and indicators of how frequently a feature is observed among the patients in the sample (Reach). The equation below depicts such a calculation.

$$\text{Fitness} = w_1 * \text{Adj Odds Ratio} + w_2 * \text{Gini Index} + w_3 * \text{ANOVA} + w_4 * \text{Reach}$$

The weights $w_1$, $w_2$, $w_3$, $w_4$ can be arrived at by pre-training the meta-learning model across different instances of predictions.

In some embodiments, a machine learning model can be trained and executed to predict a likelihood that at least one feature generated or selected by the feature generation model 115 would contribute to the prediction of an event (e.g., have a non-zero feature importance score). In some implementations, the machine learning model can be an extreme gradient boosting (XGBoost) model that classifies selected features by the feature generation model 115 to features with a zero feature importance score and features with a non-zero feature importance score. The XGBoost model can include a set of hyperparameters such as, for example, a number of boost rounds that defines the number of boosting rounds or trees, maximum depth that defines a maximum number of permitted nodes. In some instances, using the machine learning model can help refine selected features.

Although the prediction device 110, the user device 160, the endpoint computer device 180, and the server device 170 are shown and described as singular devices, it should be understood that, in some embodiments, one or more prediction devices, one or more user devices, one or more endpoint computer devices, and/or one or more server devices can be used in the prediction system 100.

FIG. 2 is a flowchart illustrating a method 200 for predicting patient journey events, according to an embodiment. The method 200 can be performed by a processor of a prediction device (such as the processor 113 of the prediction device 110 as shown and described with respect to FIG. 1). The method 200 can include receiving, at 201, high dimensional patient data that include a set of base features. The set of base features can include information about the patient journey events including, for example, a doctor visit(s), a lab test(s), a pharmacy prescription(s), a hospitalization record(s), a diagnosis(es), a medication(s), a procedure(s) and/or the like. For example, the patient journey events can include a doctor visit instance that contains information about a reason(s) for the visit, a symptom(s), a proposed medication(s), a future visit schedule(s), and/or the like.

The method 200 can include associating, at 202, an occurrence probability to each base feature of the high dimensional patient data to generate a set of profiled base features. Doing so can improve the chances of selection of base features from the set of base features that more frequently appear in the patient journey events. In some implementations, occurrence frequencies of the base features in the high dimensional patient data can be determined and an occurrence distribution of the base features can be generated. The occurrence probability for each base feature from the set of base features can be calculated in reference to the occurrence distribution of the set of base features to generate the set of profiled base features. In some implementations, the selection probability of the set of base features in the high dimensional patient data can be determined based on past feature generations or selections and a selection probability distribution of the set of base features can be generated. In such implementations, the selection probability for each base feature can be calculated in reference to the selection distribution of the set of base features and the selection probability can be used instead of occurrence probability to generate the set of profiled base features. In some instances, the occurrence probability and/or the selection probability can be described as a normalized number between 0 and 100, between 0 and 1, and/or the like.

The method 200 can include executing, at 203, a time search model to select at least one-time interval from a set of time intervals, each time interval rolling up and/or aggregating a subset of profiled base features from time intervals associated with such base features. The time search model can be and/or can include a hierarchical time search. The hierarchical time search can involve selecting time intervals in granular levels. Each granular level can be indicative of a level of details for base features considered in the time search model. In some instances, a higher level of details can be considered in more granular levels.

The method 200 can include executing, at 204, a feature generation model to select at least one feature from the set of profiled base features, the feature generation model including and/or accessing a feature store. In some implementations, the feature generation model can include a genetic algorithm. In some implementations, the feature store can include a memory allocation to store previously selected features. Therefore, the feature store can prevent/reduce the generation of duplicate features. For example, the feature store can record features considered in iterations of the genetic algorithm such that in subsequent iterations of the genetic algorithm the feature being considered is not the same as a previously considered feature. Specifically, by comparing a feature under potential consideration with features considered in previous iterations, the genetic algorithm can ensure that the feature under consideration has not yet been considered and reduce redundancy. Doing so can help the convergence of the genetic algorithm by not using storage and/or computing resources to consider redundant features. Moreover, profiling the set of base features to generate the set of profiled base features described above can substantially reduce the selection time of the genetic algorithm by starting with a base feature that has a high likelihood of being a good predictor of the patient journey events.

The method 200 can include executing, at 205, a meta-learning model (such as the fitness calculator 117 as shown and described with respect to FIG. 1) to calculate a fitness score based on at least one feature and the at least one-time interval. The meta-learning model can calculate multiple scores, each evaluating at least one feature and/or at least one-time interval. In some instances, the multiple scores can include an adjusted odds ratio (as described above with respect to FIG. 1), a statistical measure of distribution (e.g., a Gini index), an analysis of variance (ANOVA) score, and/or the like. The method 200 can further include executing, at 206, a classifier (e.g., XGBoost model) to predict an importance score for the at least one feature. The acts performed as part of a disclosed method 200 can be ordered in any suitable way. Accordingly, embodiments can be constructed in which processes or steps are executed in an order different than illustrated, which can include performing some steps or processes simultaneously, even though shown as sequential acts in illustrative embodiments.

While not shown in FIG. 2, after predicting an importance score for the at least one feature, important features can be selected based on their importance scores and used to predict an event in the patient's journey. In some implementations, for example, the selected features can then be provided as inputs to a machine learning classifier and/or a predictive model (e.g., an XGBoost, Random Forest, neural network, and/or the like) that can use the selected features to predict future events. Such a classifier and/or predictive model can be trained using supervised learning (e.g., using labeled training data of events) and/or unsupervised learning (e.g., to identify patterns of prior events using unlabeled data). Because the inputs to the classifier and/or predictive model are the features selected by the method of feature generation or selection described herein, an output of the classifier and/or predictive model has a higher likelihood to occur than a prediction performed based on the base features. In some embodiments, at least one feature can be presented to a user of the prediction device, a user of the user device, and/or a user of the endpoint computer device to determine and/or predict a future event in a patient's journey based on the at least one feature.

Figure 3:
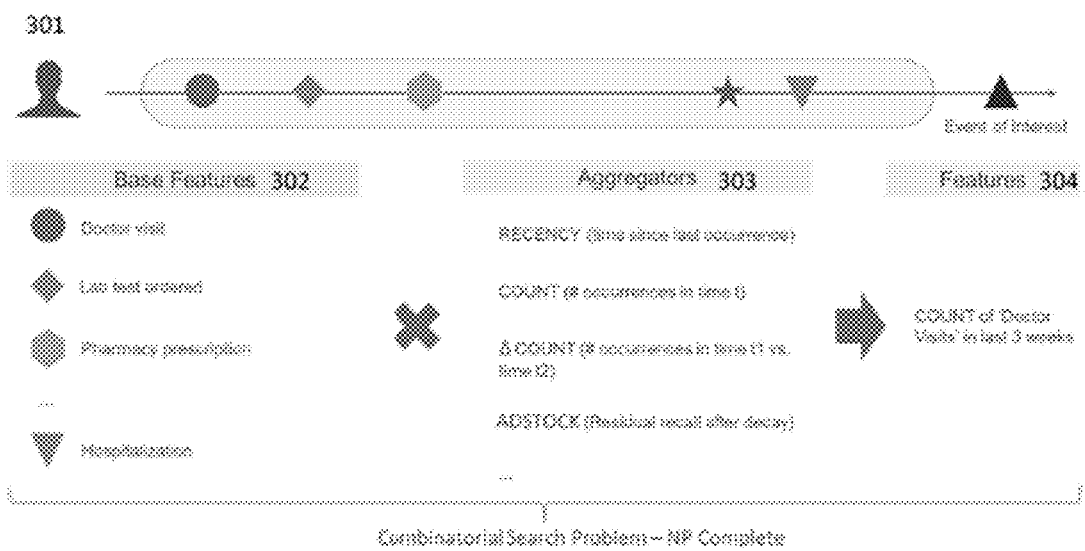
FIG. 3 is a schematic description of feature selection, according to an embodiment.

FIG. 3 is a schematic description of feature generation, according to an embodiment. A process of feature generation or selection can be and/or can include a combinatorial search process in which combinations of base features 302 and data aggregators 303 (also referred to as 'aggregators') can be selected for a patient 301 using a prediction device (such as the prediction device 110) and/or a user device (such as the user device 160) operatively coupled to the prediction device. The data aggregators can include functions, models, and/or objects that roll up and/or aggregate base feature occurrences across time intervals. For example, the data aggregators can include a recency aggregator that indicates a time since the last occurrence of a base feature. In another example, the data aggregators can include a count aggregator that indicates the number of occurrences of a base feature in a predetermined and/or selected time interval. In another example, the data aggregators can include a delta count aggregator that indicates a difference in the number of occurrences of a base feature in a first time period compared to a number of occurrences of a base feature in a second time period.

In some instances, the base features 302 can include information about a patient 301 including, for example, a doctor visit(s), a lab test order(s), a pharmacy prescription(s), a hospitalization record(s), and/or the like. In some instances, the process of feature generation or selection can involve executing a genetic algorithm (GA) for the combinatorial search. The parameters of the GA (e.g., a maximum number of generations, fitness threshold, etc.) are decided based on heuristics observed across several executions of the GA. The GA selects features 304 based on a combination of the base features 302 and the aggregators 303. For example, the GA can select a base feature 302 of 'doctor visit' with an aggregator 303 (time interval aggregator) of 'count in the last 3 weeks' to generate a feature 304 of 'count of doctor visits in last 3 weeks.' The feature 304 can be presented to a user of the prediction device as the output of the process of feature generation and/or can be used as an input to a classifier to identify future patient events.

Figure 4:
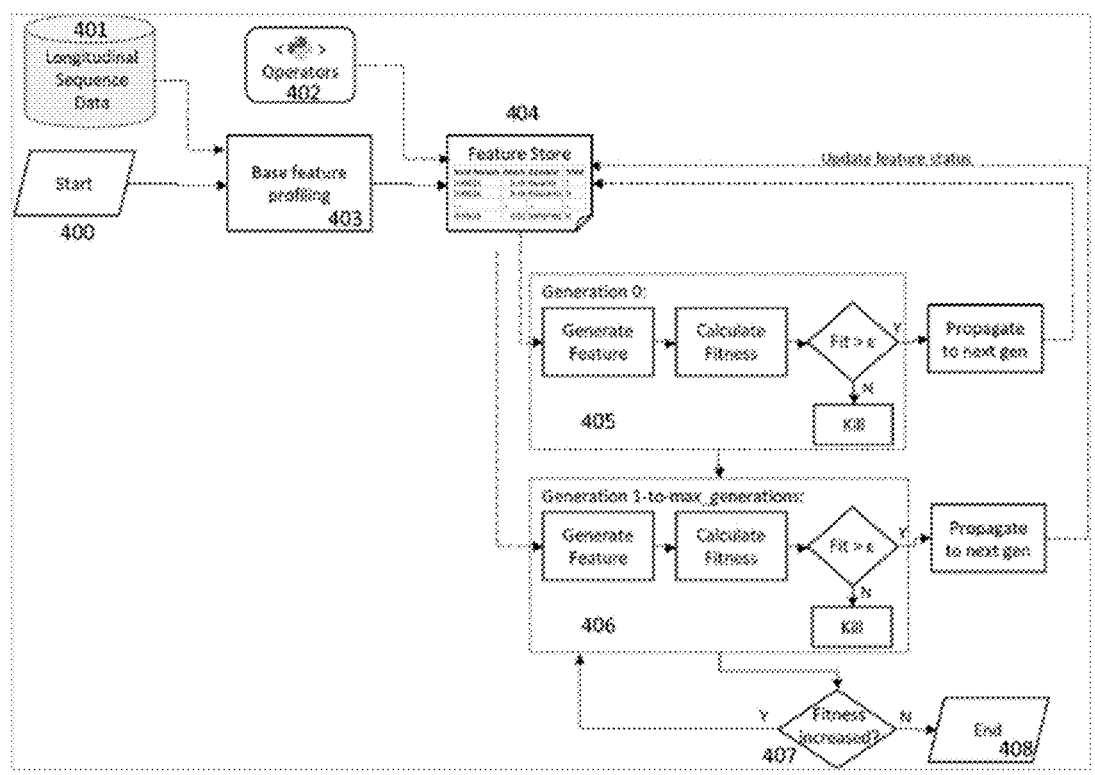
FIG. 4 is a flowchart illustrating a method of feature selection, according to an embodiment.

FIG. 4 is a flowchart illustrating a method of feature generation, according to an embodiment. The method of feature generation can involve executing a feature generation model (such as the feature generation model 115 as shown and described with respect to FIG. 1). As shown in FIG. 4, the feature generation model can be and/or can include a genetic algorithm model. The feature selection model can start 400 the method of feature generation upon an indication of interest to predict a patient journey event by a prediction device (such as the prediction device 110), a user device (such as the user device 160 operatively coupled to the prediction device 110) and/or an endpoint computer device (such as endpoint computer device 180 operatively coupled to the prediction device). The feature generation model receives longitudinal sequence data 401 (e.g., high volume and high dimensional data) including base features.

The feature generation model uses base features profiling 403 to associate a selection probability and/or an occurrence probability to each base feature to generate profiled base features. A subset of profiled features (a feature that is associated with a selection/occurrence probability) can be selected and combined with an operator 402 and a time window to generate model features and store the model features at a feature store 404 (e.g., in a memory) based on a selection criterion. The generated model features are evaluated for fitness and those features that have a fitness score greater than a threshold are selected for further refinement (e.g., mutation) and the rest are discarded as low fitness features. In some instances, the threshold can be an empirically determined threshold or a theoretically determined threshold.

Features can be generated and evaluated at an initial generation function 405 and/or a generation function 406 using a combination of an operator 402, a base feature, and a time window. Multiple features (e.g., the population of model features) can be generated in each iteration of the genetic algorithm model. The initial generation function 405 can involve calculating first fitness scores for the features and assessing whether the first fitness scores of the features meet a first criterion (e.g., being larger than a threshold). The fitness score can be evaluated for fitness using the calculation that involves adjusted odds ratio, statistical measures like Gini index and/or ANOVA, and also the observed occurrence of base feature among patients.

When a feature's fitness score is greater than a threshold, the feature can be deemed fit and can propagate to the next iteration (or generation) of the genetic algorithm model while the rest are discarded as low fitness features. In other words, when the features do not meet the first criterion, the features can be removed, killed, and/or discarded. When the features meet the first criterion, the status of the feature can be updated in the features store 404. The propagated features can be then refined by making changes to the time window (e.g., mutation). Refining the time window can be performed using a hierarchical time search model. As the initial iteration starts at the highest level of time (e.g., year), the hierarchical search traverses through the lower levels of granularity (e.g., semester then quarter then month then week then day). In any of these steps, if the fitness of the mutated or modified time window becomes less than the parent feature, the mutation process is terminated, and the feature generation is rolled back to the parent feature.

The generation function 406 can involve calculating a second fitness score for the features and assessing whether the second fitness score of the feature meets a second criterion (e.g., being larger than a threshold). The first fitness score and/or the second fitness score can be recorded and a fitness trend of the first fitness score and/or the second fitness score can be evaluated in a fitness evaluation function 407. The fitness evaluation function 407 can determine whether to continue or end iterations of the feature generation model based on the fitness trend. When the fitness trend indicates improvement, the feature generation model can continue to iterate for further improvement across additional generation functions. When the fitness trend indicates a lack of improvement, the feature generation model ends at 408. At each iteration, after generating, each feature is registered in the feature store 404 to keep track of combinations that have been already tried. Therefore, the genetic algorithm model can be more efficient than genetic algorithms that do not use the feature store 404, by not duplicating features that have already been discarded in prior iterations.

At the end 408 of the method of feature generation, the final set of model features that passed the fitness criteria can be leveraged for predicting events in a patient's journey. In some embodiments, a predictive model (e.g., a gradient boosted tree, a neural network, a random forest, a logistic regression, and/or the like) can be used on the set of features to predict a future event in the patient's journey. Since the predictive model is executed on the set of features selected by the method of feature generation described above, the predictive model performance has a higher likelihood to be better than a prediction performed based on the base features.

In some embodiments, the set of features can be presented to a user of the prediction device, a user of the user device, and/or a user of the endpoint computer device to determine a future event in a patient's journey based on the set of features. In an example, the set of features can be used to inform a clinician about a certain disease or event risk for patients and alert the clinician to take appropriate action. In another example, the set of features can be used to inform a pharma marketer or sales representative which doctor is likely to have a patient of interest (e.g., a patient who is likely to have a specific event of interest) and use information about the patient of interest for sales detailing/messaging. In another example, the set of features can be used to inform a pharma clinical trial site selection team to identify the patients who are likely going to have a specific event of interest to the managing doctor. Yet in another example, the set of features can be used to inform a health plan about the potential risk of diseases/events for members of the health plan and alert the members to take appropriate preventive actions.

Figure 5:
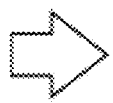
FIG. 5 is a schematic description of feature profiling for patient journey event prediction, according to an embodiment.

FIG. 5 is a schematic description of base feature profiling for patient journey event prediction, according to an embodiment. The base feature profiling can be performed by a data profiler (such as the data profiler 114 as shown and described with respect to FIG. 1). The data profiler can associate a selection probability to each base feature from base features 501 of a high dimensional patient data to generate profiled base features 502. The feature profiling described can be performed at base feature profiling 403 as shown and described with respect to FIG. 4. Doing so can improve the chances of selection of base features that are more likely to predict patient journey events. In some instances, the selection probability can be described as a normalized number between 0 and 1. In some implementations, the base features 501 can be initially associated with a default selection probability value (e.g., 0.001). After executing the data profiler and generating the profiled base features 502, each profiled base feature can be associated with an updated probability value. For example, base features identified by Dx0001 and Px3409 indicators can have an identical default selection probability of 0.001 at the beginning. After profiling the base features, the profiled base features identified by the same Dx0001 and Px3409 indicators can have selection probabilities of 0.09 and 0.03, respectively. Consequently, the profiled base feature Px3409 having a selection probability of 0.09 is more likely to be selected as a feature by a feature generation model than the profiled base feature Dx0001 that has a selection probability of 0.03. After the base feature profiling, the profiled base features 502 or a subset of the profiled base features 502 can be stored in a feature store (such as the feature store 404 as shown and described with respect to FIG. 4).

Figure 6:
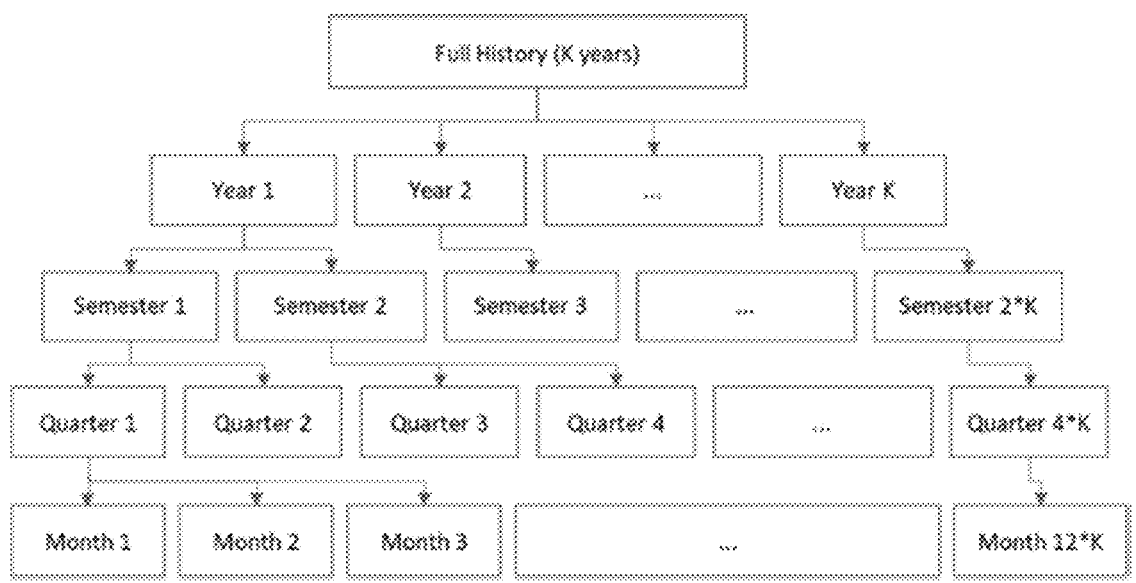
FIG. 6 is a schematic description of time interval selection for patient journey event prediction, according to an embodiment.

FIG. 6 is a schematic description of hierarchical time interval selection for patient journey event prediction, according to an embodiment. The time interval selection can be performed by a hierarchical time search model (such as the time search model 116 as shown and described with respect to FIG. 1) on patient journey event data that has a temporal nature. In some instances, the patient journey events data can include time series such as, for example, body temperature, cardiovascular activity, neural activities, and/or the like. In some instances, the patient journey events data can include events that occur over time. The time intervals in the hierarchy span across different levels of granularity, for example, a year(s), a semester(s), a quarter(s), a month(s), a week(s), a day(s), an hour(s), a minute(s), a second(s), a millisecond(s), and/or the like. The hierarchical time search model can select at least one time interval from a set of time intervals, each time interval rolling up a base features and/or profiled base features (e.g., profiled by occurrence probability and/or selection probability).

The hierarchical time search model can involve selecting time intervals in granular levels of the patient journey events data, each granular level indicating a level of details considered in the time search model. In some implementations, hierarchical time search can be/include a binary tree search that propagates across the granular levels of the patient journey events data. Using temporal granularity of the patient journey events data can significantly reduce a number of iterations needed for convergence of the hierarchical time search model for selecting the at least one time interval.

While, in some embodiments, a prediction device (such as the prediction device 110 as shown and described with respect to FIG. 1) is used to predict a patient's journey events, the prediction device can be also used to predict other types of events. In some embodiments, the prediction device can predict a career path event based on high dimensional data of individuals including education history, professional experience data, community affiliation data, social connection trees, and/or the like. In some embodiments, the prediction device can predict a natural disaster event based on high dimensional data including geological data, seismic data, climate data, and/or the like. In some embodiments, the prediction device can predict a purchasing event based on high dimensional client data including social data, purchase history data, financial data and/or the like.

FIG. 7 depicts a flowchart illustrating a method 700 for predicting patient journey events, according to an embodiment. The method 700 can be performed by any processor or computer discussed and/or shown herein, for example, in FIG. 1. For instance, the method 700 can be performed by a processor of a prediction device (such as the processor 113 of the prediction device 110 as shown and described with respect to FIG. 1), a processor of the user device 160, the server device 170, and/or the endpoint computer device 180.

In some configurations, one or more steps of the method 700 may be performed by different computing devices discussed herein. For instance, a processor of the prediction device 110 may perform one or more steps of the method 700 and a processor of the user device 160, the server device 170, and/or the endpoint computer device 180 may perform one or more other steps of the method 700.

Moreover, the method 700 is not limited to the depicted order. For instance, one or more of the steps of the method 700 may be performed in a different order and at different times. Therefore, the method 700 may be performed partially and asynchronously (or sometimes synchronously) by different computer devices discussed herein. For instance, one or more steps may be performed while training an artificial intelligence model to predict an event associated with patients (also known as a patient event or a patient journey event) using patient data included within a high dimensional dataset. Accordingly, one or more steps may be performed at prediction time by a processor of the prediction device or the user device.

In a non-limiting example, the prediction device 110 embodies a software as a service (SaaS). For instance, when a user device inputs a request to view a predicted event associated with a patient, the prediction device 110 may perform various steps of the method 700 to analyze a high dimensional dataset associated with the patient and generate a prediction. In that example, the method 700 may be performed at prediction time. In another non-limiting example, the prediction device 110 may use the method 700 to select a set of features to be used to train an artificial intelligence model. In that example, the method 700 may be performed before prediction time. Various embodiments and synchronous/asynchronous execution of different steps can occur and do not deviate from the scope of the method 700.

At step 701, the processor may profile one or more features within a high dimensional patient dataset in accordance with their respective probability of occurrence. The processor may determine a probability of occurrence of one or more features within the high dimensional patient dataset and profile the one or more features in accordance with their respective probability of occurrence.

The processor may retrieve a dataset that includes high dimensional data associated with a patient. For instance, the dataset may include patient information (e.g., features) corresponding to the patient journey events including, for example, a doctor visit(s), a lab test(s), a pharmacy prescription(s), a hospitalization record(s), a diagnosis(es), a medication(s), a procedure(s) and/or the like. For example, the patient journey events may include a doctor visit and may contain information about a reason(s) for the visit, a symptom(s), a proposed medication(s), a future visit schedule(s), and/or the like.

The processor may first calculate a probability of occurrence for different features within the high dimensional dataset and may profile the features based on their corresponding probability of occurrence. In a non-limiting example, the data profiler 114 depicted in FIG. 1 may perform this step. The processor may calculate or identify a frequency of occurrence for each feature within the dataset. Consequently, the processor may calculate an occurrence probability for different features within the dataset. If the probability of occurrence or the frequency of occurrence for each event/data/feature satisfies a predetermined threshold, the processor may profile (select) said feature. That is, the processor may reduce the number of features within the high dimensional dataset by filtering the features based on their corresponding probability of occurrence and/or frequency of occurrence. In this way, the processor can reduce the patient data to a selected profiled subset of the data with a high likelihood of being a good predictor of the patient journey events.

The processor may assume that data associated with an event or feature is a good candidate to be analyzed by a computer model to predict a patient event because it occurs more frequently than other events and/or features. In effect, the processor may eliminate outliers and events that rarely occur or have a low likelihood of occurrence in the future. A non-limiting example of profiling one or more features based on their frequency of occurrence or probability of occurrence is depicted in FIG. 5.

Referring back to FIG. 7, at step 702, the processor may select at least one feature from the profiled features and the corresponding time window for the at least one feature. The processor may execute a feature generation model to select at least one feature from the profiled features (step 701) and a corresponding time window for the at least one feature.

The processor may execute a feature generation model that selects one or more features within the profiled set of features. In some configurations, the processor may execute the feature generation model 115 to select a subset of features from the profiled features (steps 701). The feature generation model can include a genetic algorithm that analyzes each feature within the profiled features based on their respective attributes, such as a maximum number of generations, a fitness threshold, and the like. The processor may down-select the profiled features in accordance with their importance using this genetic algorithm. Once at least one feature within the profiled features is identified by the feature generation model, the processor may store the identified feature within a feature store (e.g., a particular location within a data repository allowing quick access to the feature).

At step 703, the processor may select at least one time interval associated with the profiled features or the at least one feature. The processor may execute a time search model to select at least one time interval from a set of time intervals that includes time intervals associated with the profiled features or the at least one feature.

The features within the profiled features may correspond to different time intervals or time stamps. As described herein, various features may have associated temporal attributes. For instance, a patient's blood pressure may also include a timestamp (e.g., a time associated with the reading). Therefore, the patient's blood pressure includes a time series, such as a chart of the patient's blood pressure readings throughout months. The processor may analyze various time intervals that include the feature (e.g., blood pressure) to identify the best time interval that would/could lead to an accurate and efficient prediction. In other words, the processor can identify a time interval that includes enough data points that, when analyzed, would allow a computer model to predict an event associated with the patient.

In the blood pressure example, the patient's blood pressure can theoretically be analyzed in its entirety (e.g., starting from the first data point indicating the patient's blood pressure within the dataset) for an accurate prediction associated with the patient. However, this brute force method of analyzing every data point may not be efficient due to the large number of data points and possible permutations. As a result, the processor may execute the time search model discussed herein to identify an appropriate time interval associated with the patient's blood pressure. The time interval selected by the processor may include enough data points that would allow the computer model to predict an accurate event associated with the patient. For instance, the processor may determine that instead of analyzing the patient's entire blood pressure history, a computer model can analyze the patient's blood pressure for the last three months.

In order to select/identify the time interval, the processor may utilize the time search model 116 depicted in FIG. 1. Furthermore, a non-limiting example of hierarchical time intervals and the operation of the time search model 116 is depicted in FIG. 6.

Referring back to FIG. 7, at step 704, the processor may calculate a fitness score based on the selected at least one feature and/or the at least one time interval. The processor may execute a meta-learning model to calculate a fitness score based on the at least one feature and the at least one time interval.

After (i) down-sampling the features into a set of profiled features, (ii) further down-sampling the set of profiled features using the feature generation model, and (iii) after identifying an ideal time interval associated with the features, the processor may calculate a fitness score based on the identified feature and the time interval. The processor may use the fitness calculator 117 depicted in FIG. 1 to generate a fitness score for the identified feature.

The processor may calculate the fitness score by executing a meta-learning model. The meta-learning model may use various analytical protocols to generate the fitness score. In one example, the meta-learning model may identify an adjusted odds ratio to evaluate a relative fitness of a feature. In another example, the fitness score can be calculated as a weighted average of multiple scores including the adjusted odds ratio, statistical information gain measures at a feature level (e.g., Gini index, Analysis of Variance (ANOVA), etc.) and indicators of how frequently a feature is observed among the patients in the sample (Reach).

In some embodiments, the processor may use a machine learning model to predict a fitness score associated with each feature in light of its corresponding time interval. For instance, the machine learning model can be trained and executed to predict a likelihood that at least one feature generated or selected (step 702) would contribute to the prediction of an event (e.g., have a non-zero feature importance score).

At step 705, the processor may use the at least one feature to predict an event associated with the patient when the at least one feature satisfies a threshold. The processor may use, responsive to the at least one feature having the fitness score that satisfies a threshold, the at least one feature to predict an event associated with a patient.

The processor may execute a computer model to predict an event associated with the patient using features (and their corresponding time intervals) that have a fitness score that satisfies a threshold. Once fitness scores are calculated, the processor may iteratively generate a list of features that satisfy a threshold. A non-limiting example of this process is depicted and discussed in FIG. 5. Once the processor down-samples the features using their corresponding fitness scores, the processor may use those features to predict an event associated with the patient. In some embodiments, the processor may execute a computer model (e.g., a computer model having predictive capabilities that use artificial intelligence modeling techniques) that ingests the features selected based on their fitness score and predicts one or more events. In some configurations, the list of features that satisfy the threshold may be used by the processor to train an artificial intelligence model (instead of using the high dimensional dataset in its entirety for training). Using a smaller training dataset, the processor can improve the training efficiency and timing.

Non-Limiting Example

A processor receives a request to predict an event associate with a patient, such as whether to recommend a medical check-up for the patient. The processor queries and receives data associated with the patient, such as data associated with the patient's EHR. The data retrieved may include features that can be used to predict the event (e.g., whether to recommend a check-up for the patient within the next two months). However, the data retrieved is voluminous and high dimensional because it includes all data associated with each doctor visit, lab results, hospitalization, medication, historical medical records, financial records, and/or social records of a patient.

Instead of executing a predictive computer model that can analyze data and generate/predict a check-up recommendation using all the data retrieved, the processor first profiles the features included within the retrieved data based on their probability/frequency of occurrence. For instance, the processor selects features that have a probability/frequency of occurrence that satisfies a predefined threshold (e.g., more than 70% probability of occurrence or has occurred more than a predefined number of times in the past three months). Each feature that satisfies the threshold may also include a corresponding timestamp or a time window.

Once the features are profiled, the processor may execute a time search model and a feature selection model to identify a subset of the profiled features and their corresponding time interval to be analyzed by the predictive computer model. For instance, the processor identifies the patient's lab data (e.g., cholesterol level and blood pressure) from the last three months as possibly important features to be analyzed. The processor then executes a meta-learning model to generate a fitness score for the patient's cholesterol level and blood pressure. When the fitness scores satisfy a fitness score threshold, the processor executes the predictive computer model and predicts/generates the patient's check-up recommendation based on the patient's cholesterol level and blood pressure for the last three months.

It should be understood that the disclosed embodiments are not representative of all claimed innovations. As such, certain aspects of the disclosure have not been discussed herein. Alternate embodiments may not have been presented for a specific portion of the innovations or that further undescribed alternate embodiments may be available for a portion is not to be considered a disclaimer of those alternate embodiments. Thus, it is to be understood that other embodiments can be utilized and functional, logical, operational, organizational, structural and/or topological modifications may be made without departing from the scope of the disclosure. As such, all examples and/or embodiments are deemed to be non-limiting throughout this disclosure.

Some embodiments described herein relate to methods. It should be understood that such methods can be computer implemented methods (e.g., instructions stored in memory and executed on processors). Where methods described above indicate certain events occurring in certain order, the ordering of certain events can be modified. Additionally, certain of the events can be performed repeatedly, concurrently in a parallel process when possible, as well as performed sequentially as described above. Furthermore, certain embodiments can omit one or more described events.

All definitions, as defined and used herein, should be understood to control over dictionary definitions, definitions in documents incorporated by reference, and/or ordinary meanings of the defined terms.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using Python, Java, JavaScript, C++, and/or other programming languages and software development tools.

The drawings primarily are for illustrative purposes and are not intended to limit the scope of the subject matter described herein. The drawings are not necessarily to scale; in some instances, various aspects of the subject matter disclosed herein can be shown exaggerated or enlarged in the drawings to facilitate an understanding of different features. In the drawings, like reference characters generally refer to like features (e.g., functionally similar and/or structurally similar elements).

The acts performed as part of a disclosed method(s) can be ordered in any suitable way. Accordingly, embodiments can be constructed in which processes or steps are executed in an order different than illustrated, which can include performing some steps or processes simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What I claim is:

1. A method comprising:
   determining, by a processor, a probability of occurrence of one or more features within a high dimensional patient dataset;
   profiling, by the processor, the one or more features in accordance with their respective probability of occurrence;
   executing, by the processor, a feature generation model to select at least one feature from the profiled features and a corresponding time window for the at least one feature;
   executing, by the processor, a time search model to select at least one time interval from a set of time intervals that includes time intervals associated with the profiled features or the at least one feature;
   executing, by the processor, a meta-learning model to calculate a fitness score based on the at least one feature and the at least one time interval;
   using, by the processor, responsive to the at least one feature having the fitness score that satisfies a threshold, the at least one feature to predict an event associated with a patient; and
   training, by the processor, a neural network using the profiled features, the corresponding time windows, and the fitness score that satisfies the threshold.

2. The method of claim 1, further comprising:
   executing, by the processor, a classifier to predict an importance score for the at least one feature.

3. The method of claim 1, further comprising:
   training, by the processor, a machine learning model to predict an importance score for the at least one feature.

4. The method of claim 1, wherein the feature generation model comprises a feature store configured to store the at least one feature.

5. The method of claim 1, wherein the meta-learning model iteratively calculates the fitness score for the at least one feature for each time interval within the set of time intervals.

6. The method of claim 1, wherein the high dimensional patient dataset comprises data associated with one or more patient journey events comprising at least one of a doctor visit, a lab test, a pharmacy prescription, a hospitalization record, a diagnosis, a medication, or a procedure associated with the patient.

7. The method of claim 1, wherein the feature generation model uses a recency aggregator indicating a time since last occurrence of the at least one feature within the high dimensional patient dataset.

8. The method of claim 1, wherein the feature generation model uses a count aggregator indicating a number of occurrences of the at least one feature within the high dimensional patient dataset.

9. The method of claim 1, wherein the feature generation model comprises a genetic algorithm.

10. A computer system comprising:
    a server having a processor to communicate with a data repository storing a high dimensional patient dataset, the server configured to:
    determine a probability of occurrence of one or more features within the high dimensional patient dataset;
    profile the one or more features in accordance with their respective probability of occurrence;
    execute a feature generation model to select at least one feature from the profiled features and a corresponding time window for the at least one feature;
    execute a time search model to select at least one time interval from a set of time intervals that includes time intervals associated with the profiled features or the at least one feature;
    execute a meta-learning model to calculate a fitness score based on the at least one feature and the at least one time interval;
    use, responsive to the at least one feature having the fitness score that satisfies a threshold, the at least one feature to predict an event associated with a patient; and train a neural network using the profiled features, the corresponding time windows, and the fitness score that satisfies the threshold.

11. The computer system of claim 10, wherein the server is further configured to execute a classifier to predict an importance score for the at least one feature.

12. The computer system of claim 10, wherein the server is further configured to train a machine learning model to predict an importance score for the at least one feature.

13. The computer system of claim 10, wherein the feature generation model comprises a feature store configured to store the at least one feature.

14. The computer system of claim 10, wherein the meta-learning model iteratively calculates the fitness score for the at least one feature for each time interval within the set of time intervals.

15. The computer system of claim 10, wherein the high dimensional patient dataset comprises data associated with one or more patient journey events comprising at least one of a doctor visit, a lab test, a pharmacy prescription, a hospitalization record, a diagnosis, a medication, or a procedure associated with the patient.

16. The computer system of claim 10, wherein the feature generation model uses a recency aggregator indicating a time since last occurrence of the at least one feature within the high dimensional patient dataset.

17. The computer system of claim 10, wherein the feature generation model uses a count aggregator indicating a number of occurrences of the at least one feature within the high dimensional patient dataset.

18. The computer system of claim 10, wherein the feature generation model comprises a genetic algorithm.

19. A computer system comprising:
a server comprising a processor and a non-transitory computer-readable medium containing instructions that when executed by the processor causes the processor to perform operations comprising:
determining a probability of occurrence of one or more features within a high dimensional patient dataset;
profiling the one or more features in accordance with their respective probability of occurrence;
executing a feature generation model to select at least one feature from the profiled features and a corresponding time window for the at least one feature;
executing a time search model to select at least one time interval from a set of time intervals that includes time intervals associated with the profiled features or the at least one feature;
executing a meta-learning model to calculate a fitness score based on the at least one feature and the at least one time interval;
using responsive to the at least one feature having the fitness score that satisfies a threshold, the at least one feature to predict an event associated with a patient; and
training a neural network using the profiled features, the corresponding time windows, and the fitness score that satisfies the threshold.

20. The computer system of claim 19, wherein the instructions further cause the processor to execute a classifier to predict an importance score for the at least one feature.

* * * * *